Oct. 11, 1949. C. G. DUEHRSEN Plant Pat. 880
POLYANTHA ROSE PLANT
Filed Jan. 2, 1948
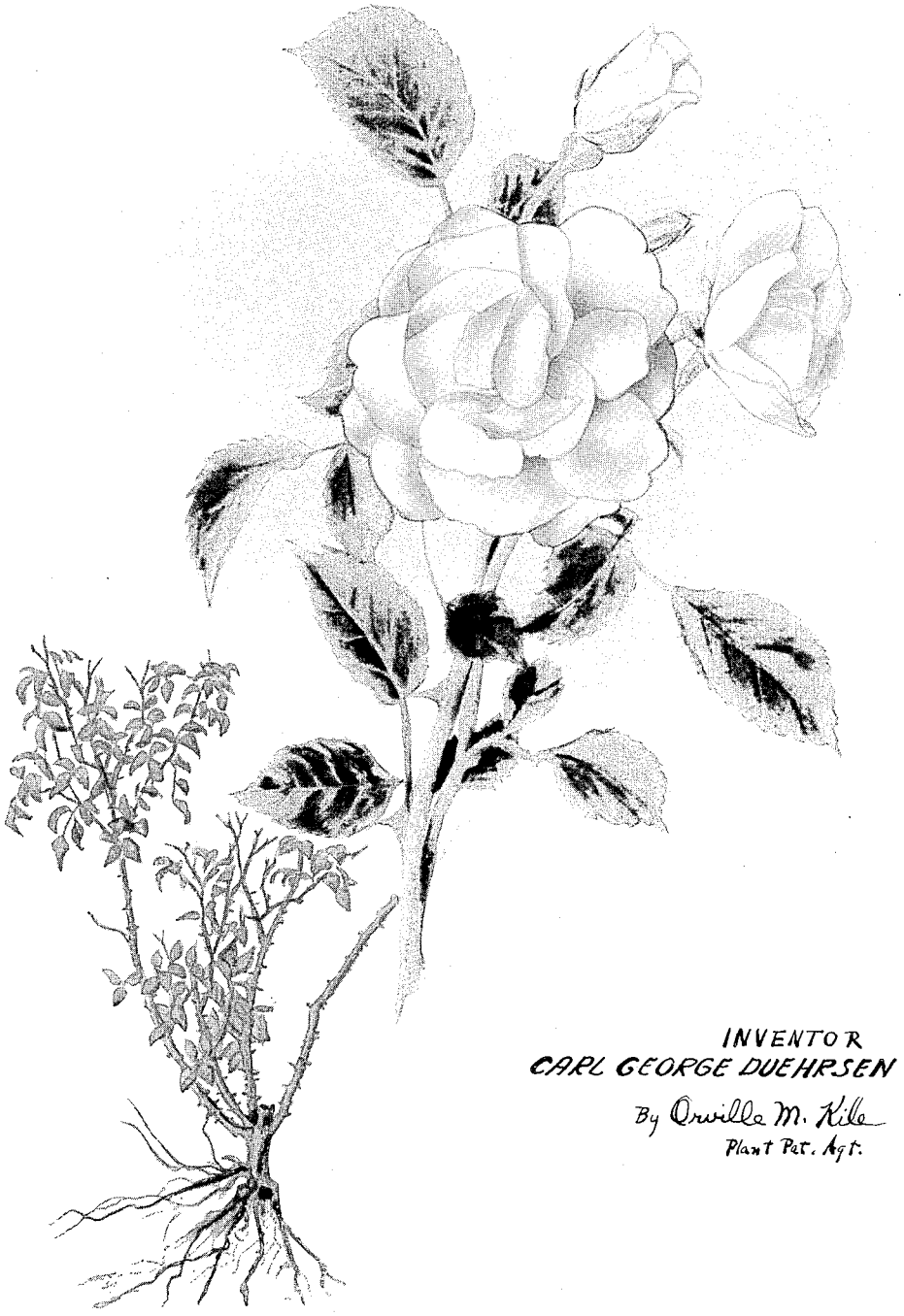
INVENTOR
CARL GEORGE DUEHRSEN
By Orville M. Kile
Plant Pat. Agt.

Patented Oct. 11, 1949

Plant Pat. 880

UNITED STATES PATENT OFFICE

880

POLYANTHA ROSE PLANT

Carl George Duehrsen, Montebello, Calif., assignor to Howard & Smith, Montebello, Calif.

Application January 2, 1948, Serial No. 108

1 Claim. (Cl. 47—61)

My present invention relates to a new and distinct variety of polyantha rose plant originating as a seedling. Its parentage is Joanna Hill by Heidekind by Betty Uprichard, but is unlike any of them.

Especially notable among its characteristics are the compactness and uniformity of its spherical growth and large semi-spherical trusses. It is splendid both for edgings in the garden and as a forcing rose. It blooms throughout the entire spring, summer and fall seasons in the open, and is amenable for use as a forcing plant under glass for winter use. So it is truly a year-round variety, producing a large number of blooms.

There is no other polyantha in its color, which is essentially white with yellow to orange tinting. It has the general character of inflorescence of the variety Pinkie but differs in many other respects.

This new variety has been asexually reproduced from cuttings in the greenhouses of Howard & Smith at Montebello, California, and its characteristics appear to be permanent.

The accompanying illustrations show in approximately true colors, three typical specimens of the bud and flower of this new variety in various stages of opening. Also small sketch indicating low compact growth.

Following is a detailed description of the plant and flower of my new variety. Plate references indicate Ridgway's Color Standards and Nomenclature. Other color references indicate the usual dictionary meaning.

*The plant*

Growth habit: Compact, low-growing and rounded, being almost spherical in general contour. Grows to a height of 12 to 18 inches. Very uniform.

Blooming habit: Remontant the year round. Flowers are borne on trusses of exceedingly large size with flowers and buds evenly distributed.

Trusses: Semi-spherical. In branching heads, the trusses are 10 to 12 inches across. Branchlets carry 6 to 8 blossoms and buds.

Disease resistance: Immune to mildew or other known diseases.

Stems:

*Color.*—Bright green.
*Strength.*—Very strong.
*Rigidity.*—Stiff.
*Aspect.*—Quite smooth except for thorns, which average about 3 to each internode. Thorns are about ⅛ inch long, brown in color, and downward-pointing.

Foliage:

*Number of leaflets.*—3 to 5.
*Quantity.*—Well foliaged.
*Shape.*—Long oval with sharp apex. Edge serrulate.
*Size.*—Entire leaf 3 to 3½ inches long.
*Texture.*—Leathery.

*Color.*—Glossy green.
*Leaf stem.*—Slender, usually with reddish cast.
*Stipules.*—Very narrow; about ¼ inch long.

*The flower*

Bud:

*Size.*—½ to ¾ inch long.
*Shape.*—Ovoid to long.
*Color.*—Pale lemon yellow (Pl. IV) to Primrose (Pl. XXX), with slight rosy blush at base. More white is evident as bud opens.
*Calyx and sepals.*—Simple, with deeply serrated edges. Do not reflex early.
*Peduncle.*—Short (about 1¼ inches) allowing foliage to appear close to flower. Very rigid.

Bloom:

*Borne.*—In very large, semi-spherical trusses.
*Size.*—Average 2¼ inches in diameter.
*Form.*—Loosely informal, opening flat but usually with central petals covering stamens.
*Color.*—White with yellow tints from Sulphur Yellow (Pl. V) to Martins Yellow (Pl. IV), particularly on inner petals. Grown under glass, the yellow tones become deeper and more pronounced.
*Discoloration.*—After reaching maturity, color changes to creamy white.
*Petalage.*—Average 25.
*Fragrance.*—Moderate.
*Longevity.*—Lasts well on plant or as cut flower.

Petals:

*Shape.*—Obovate.
*Aspect.*—Silky.
*Size.*—Average 1 inch from tip to base.
*Color.*—Essentially white, but with yellow shadings.
*Arrangement.*—Informal and loose.
*Texture.*—Very leathery.
*Persistence.*—Cling tenaciously.

Reproductive organs:

*Pistils.*—Greenish white.
*Stamens.*—Many, surrounding pistils. Approximately Buff-Yellow (Pl. IV).
*Ovaries.*—Sterile.

Having thus disclosed my invention, I claim:

The new and distinct variety of polyantha rose plant, substantially as herein shown and described, characterized particularly by its disease resistance; its uniform, low, compact, rounded form; its exceedingly large semicircular trusses upon which flowers and buds are evenly distributed; its easy adaptability as a forcing rose; its completely remontant blooming habit; and its loosely informal flowers which present a variety of combinations of white and yellow in various stages of opening.

CARL GEORGE DUEHRSEN.

No references cited.